United States Patent [19]

Beal

[11] 4,257,421

[45] Mar. 24, 1981

[54] GASTRO-INTESTINAL TUBE GUIDE AND STIFFENER

[75] Inventor: Charles B. Beal, Menlo Park, Calif.

[73] Assignee: Health Development Corporation, Mountain View, Calif.

[21] Appl. No.: 2,362

[22] Filed: Jan. 10, 1979

[51] Int. Cl.³ .............................................. A61M 25/00
[52] U.S. Cl. .................... 128/348; 128/341; 128/657; 128/772
[58] Field of Search .............................. 128/348–351, 128/341, 276, 214.4, 657, 772, DIG. 9

[56] References Cited

U.S. PATENT DOCUMENTS

| 2,244,027 | 6/1941 | Smith | 128/341 |
| 2,508,690 | 5/1950 | Schmerl | 128/276 |
| 2,548,602 | 4/1951 | Greenburg | 128/4 |
| 2,593,980 | 4/1952 | Calicchio | 128/276 X |
| 3,358,684 | 12/1967 | Marshall | 128/214.4 |

FOREIGN PATENT DOCUMENTS 1435797  5/1976  United Kingdom .................... 128/657

*Primary Examiner*—Dalton L. Truluck
*Attorney, Agent, or Firm*—William E. Green

[57] ABSTRACT

A device for use in inserting soft and flexible tubular devices into a body passageways, said device characterized by being formed from a flexible base, such as multiple-strand nylon thread and having deposited upon said flexible base a soluble material such as gelatin, said soluble material characterized by being less flexible than said base in its undissolved state.

5 Claims, 5 Drawing Figures

GASTRO-INTESTINAL TUBE GUIDE AND STIFFENER

BACKGROUND OF THE INVENTION

1. Field of the Invention

This invention relates to a device for use in connection with tubular structures designed for insertion into body passageways such as gastro-intestinal tracts and more particularly relates to a guide device to stiffen the tubular structure and facilitate the insertion of the tubular structure into a body passageway, to permit accurate guidance of the tubular structure within the passageway, and to provide for easy removal of the guide device after the tubular structure has been properly positioned within the passageway.

2. Description of the Prior Art

Tubular structures such as catheters, and tubes for dispensing fluids into or removing gas or fluids from blood vessels, urinary tracts, gastro-intestinal and other cavities of patients are commonly used within the healing arts.

The insertion of such tubular structures into the desired cavity of a patient often requires the negotiation of convoluted and tortuous passageways. The inconsistent requirements that such tubular structures be sufficiently flexible to negotiate the passageways and sufficiently soft to not injure the patient, but at the same time be sufficiently rigid to permit accurate guidance has spawned a plethora of devices designed for the purpose of guiding said tubular structures through the labyrinth of passageways that characterize blood vessels, gastro-intestinal and urinary tracts.

Notwithstanding the recognition in the prior art of the basic perameters necessary to provide an effective and efficient tube guide device, the need for devices combining the properties of stiffness sufficient to facilitate passage of the tubular structure, flexibility sufficient to facilitate guidance of the tubular structure and easy removability of the guide device without the risk of injury to the patient, and without pulling the tubular structure out, has not been fulfilled by prior art devices.

Although numerous patents have been issued covering tube guides, attempts to implement such tube guides in connection with tubular structures acceptable to the medical profession have been largely unsuccessful. The major reasons for such lack of success have been the inability to provide a guide that accomplishes its guide function and may then be easily removed without injury to the patient.

Prior art devices have suffered in part or in whole from various problems which are solved by this invention.

One type of prior art device consists of a teflon coated wire guide. (See publication Wire Guide and Technique for Tube Insertion American Journal of Roentgenology, Volume 107, Pages 150-155, 1969.) This article particularly cautions against leaving the guide in place as the tube enters the duodenum out of fear that the convolutions of the tube will prevent the wire from being withdrawn.

Another prior art device uses a Volkswagon Speedometer cable (see publication Rapid Duodenal Intubation using a Wire Guide), (Digest Diseases, Volume 15, Page 1099, December 1970), the author of this device also cautions against introducing the wire past the stomach for the same reasons as given above.

In the article Duodenal Intubation (see the Lancet June 10, 1972, page 1270) a tube is described in which a series of guide wires are incorporated with a control mechanism to provide guidance of the tube.

Tube insertions consisting of sets of steel wires arranged in columnar fashion and having mechanisms for expanding and contracting the circumference of the column are known.

A device in which the guide is a tube of larger diameter than the tube itself and in which the tube to be passed is positioned longitudinally within the guide tube is described in U.S. Pat. No. 3,703,174. In this device after passage the smaller tube is expelled from the guide tube by an injection of water.

Another prior art method discloses a device for passing a small flexible tube by coupling it with a larger stiffer tube through inserting the ends of each tube into a gelatine capsule. U.S. Pat. No. 3,995,628 discloses a catheter device composed of a cylindrical dispenser using a needle secured to a dispenser having a rotatable catheter receptacle to forward the catheter through the needle.

It is the primary object of this invention to provide a low cost, simple tube guide that stiffens the tube which it is desired to pass, is readily guided and is easily removed.

It is a further object of this invention to provide a tube guide that may be used in connection with feeding tubes for infants and which may be passed into the small bowel as far as the jejunum.

It is yet another object of this invention to provide a tube guide that may be used with a variety of prior art tube structures and does not require a specially designed tube structure.

It is still another object of this invention to provide a tube guide which may be rotated in a manner to increase the likelihood of locating the proper channel in which insertion is desired.

It is a still further object of this invention to provide a device for applications in which a tortuous passageway makes removal difficult and which may be partially dissolved in place leaving an easily removed residuum.

It is also an object of this invention to provide a device which may be extended externally to impinge upon a previously supplied gelatin capsule located at its distal end.

SUMMARY OF THE INVENTION

Typical prior art feeding tube fabricated from conventional rubber materials have serious disadvantages such as poor lubricity and abrasive areas at the fabrication points on the tube where plugs are used to close the distal end of the tube. Recently, methods of forming tubes from silicone elastomer material have been developed. These tubes are advantageous because of the inherent increased flexibility of the material and because of the ability to fabricate structures, such as the above referenced plugs through in situ curing in a manner that eliminates abrasive areas.

The only factor that has kept such tubes from being universally accepted has been the fact that their most advantageous property, namely flexibility, makes the tube more difficult to place and guide within the patient.

The preferred embodiment of this invention when used in conjunction with a silicone elastomer tube makes the promise of such tubes a practical reality. This advance in the art is achieved by constructing a flexible rod formed by applying USP gelatin to a multi-strand nylon thread base in a spiral twist which results in regularly recurring variations in the diameter of the rod. This rod is sized in a length and diameter to fit the tube to be inserted and inserted within such tube. The tube is then inserted into the patient cavity with the guide serving to stiffen the tube to facilitate passage. After the tube is positioned, the guide is withdrawn by injecting a few milliliters of water into the tube, which dissolves a portion of the gelatin and expedites removal of the guide. If the particular patient cavity is convoluted and the guide is not easily withdrawn, additional water may be added until the gelatin is completely dissolved leaving only the threads of nylon which are readily retractible. If it is not desirable to insert water, feeding may commence which will also result in the dissolution of the gelatin and ultimately in the easy removal of the nylon threads.

Thus the apparently inconsistent properties of stiffness for guidance and flexibility for withdrawal are provided in a single device to create a heretofore unknown but instantly welcome advance in the state of the art.

BRIEF DESCRIPTION OF THE DRAWINGS

A complete understanding of the invention may be obtained from the following description and explanation which refer to the accompanying drawings illustrating the invention.

DESCRIPTION OF THE INVENTION

Figure 1:
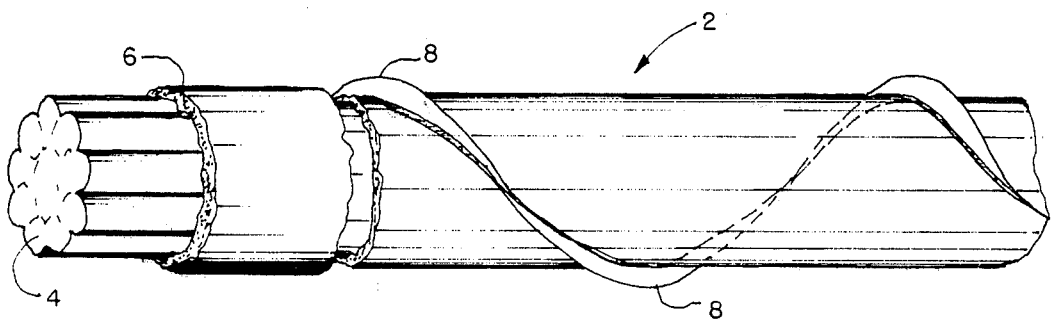
FIG. 1 is an enlarged illustrative view of a completed guide in accordance with the invention.

Referring now to FIG. 1, the basic structural components of the present invention are described. A tube guide and stiffner in accordance with the invention is generally designated as guide 2 and is formed from multiple strands of thread 4 coated with gelatin 6 in a molten state and then twisted and solidified to form minute recurring ridges 8. The cutaway portions of FIG. 1 showing threads 4 and coating 6 as distinctively separate is illustrative only as it is apparent that the uncoated threads are a transitional phase in the fabrication of guide 2.

Figure 2:
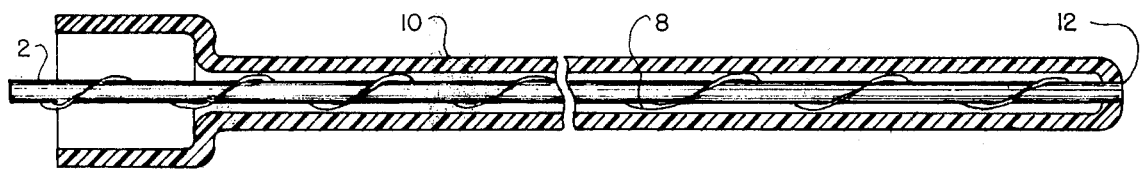
FIG. 2 is a cross-sectional view of a tube having a guide as shown in FIG. 1 inserted within said tube.

FIG. 2 shows a tube 10, which may be a gastro intestional or nasogastric tube, having a constricted distal aperture 12 of a size designed to allow the distal end of guide 2 to be frictionally fitted within aperture 12 sufficiently snugly to allow rotation of tube 10 by rotation of guide 2.

Figure 3:
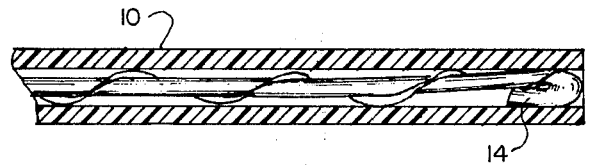
FIG. 3 is an embodiment as shown in FIG. 2, but having its distal end folded over within the tube.

FIG. 3 shows a tube 10 without a constricted distal aperture 12, but wherein guide 2 has a folded distal tip 14 to provide a snug fit within tube 10.

Figure 4:
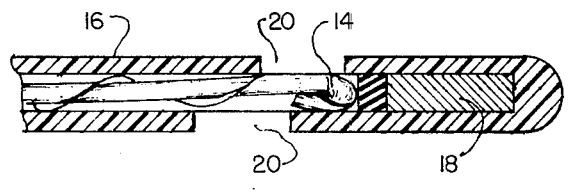
FIG. 4 is an embodiment as shown in FIG. 3 wherein the tube is of the weighted mercury type having lateral distal apertures.

FIG. 4 is yet another variation showing a weighted tube 16 containing, mercury 18 or some other weighting substance in a closed distal end and having lateral distal apertures 20, and with guide 2 having a folded distal tip 14.

Figure 5:
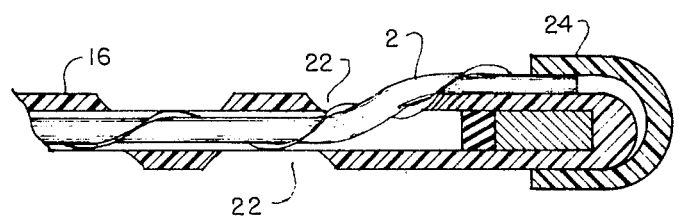
FIG. 5 shows a variation in conjunction with an external anchoring of the guide at the distal end of the tube.

FIG. 5 is a variation showing a weighted tube 16 having curved lateral distal apertures 22 and an external distal cuff 24 designed to accommodate guide 2 which is passed through apertures 22 and terminates snugly within cuff 24.

The variations described above are illustrative of the ways in which the guide disclosed herein may be used in combination with existing tubes and in all cases enhance and expand the applications for such existing tubes.

A grasp of the general concept of this invention makes it apparent that its scope is not limited to the materials disclosed but rather may be broadly described as the formation of a tube guide and stiffener by coating a flexible material with a substance having the dual characteristic of being stiffer than the flexible material in an undissolved state to facilitate passage of the tube, but readily soluble in situ to facilitate removal of the guide.

It is clear that the dimensions of the guide and the selection of the appropriate coating material are limited only by the skill of the user once the basic concept is disclosed. For example although the disclosed preferred embodiment uses a nylon thread, the use of cotton or silk threads, yarn or fine wire may be appropriate in some applications. The USP gelatin of the preferred embodiment could be replaced with other soluble stiffening materials, or gelatin may be mixed with other compatible substances, such as albumin. Other useful applications of this invention encompass the addition of radio-opaque or coloring materials to the gelatin or thread for the purpose of tracing or color-coding.

Yet another variation of the guide encompasses the use of a soluble thread made of a material such as alginite or polyvinyl alcohol.

In an application where the passageway into which the tubular device is to be inserted is of sufficient size, the guide may be attached externally to the tube. In such an application the tube need not be hollow, but may be a solid catheter, for example.

The guide of the present invention as described in the preferred embodiment is fabricated by the application of gelatin in its molten state to vertically disposed strands and then twisting such strands by rotating them at their distal ends as the gelatin hardens to form a twisted strand guide having a rope like texture. The spiral construction keeps the device from warping both while drying and during storage before use and the varied surface facilitates rotation for insertion or removal of the guide. The determination of the process times and temperatures is believed to be within the skill of the art once the basic process is disclosed, however a typical embodiment is fabricated as follows: 150 grams of Gelatin are dissolved in 100 ml water and heated until the solution clears. Uncoated nylon threads are pulled through the Gelatin and allowed to hang vertically with a weight on the lower end. The weight is spun to twist the guide until approximately 1 twist per inch is achieved and the device is allowed to dry.

While the embodiments described and illustrated may be modified in various ways readily apparent to those skilled in the art, the invention is intended to include those within the spirit and scope of the following claims.

What is claimed is:

1. A guide for introducing a tubular device into a selected body passageway comprising an elongated core member of flexible base material consisting of a plurality of threads and a soluble coating on said base material, said coating characterized in its undissolved state by being less flexible than said tubular device flexible base material.

2. A guide according to claim 1 wherein said base material consists of a plurality of nylon threads.

3. A guide according to claim 1 wherein said base material consists of a plurality of nylon threads and said soluble coating is USP gelatin.

4. A guide according to claim 3 wherein said soluble coating is characterized by having a plurality of areas of slightly enlarged diameter.

5. A method for making a guide for inserting a tubular device into a selected body passageway consisting of coating a flexible base material comprising a plurality of threads with a less flexible soluble material while twisting said threads, to form a plurality of areas of said guide of slightly enlarged diameter.

* * * * *